United States Patent [19]  
Lau et al.

[11] Patent Number: 4,978,790  
[45] Date of Patent: Dec. 18, 1990

[54] 4,4′-BIS[2-(4-HYDROXY-AMINO-PHENYL)-HEXAFLUOROISOPROPYL]-DIPHENYLETHERS AND THEIR USE

[75] Inventors: Jürgen Lau; Günter Siegemund, both of Hofheim am Taunus, Fed. Rep. of Germany

[73] Assignee: Hoechst Aktiengesellschaft, Frankfurt am Main, Fed. Rep. of Germany

[21] Appl. No.: 276,194

[22] Filed: Nov. 23, 1988

[30] Foreign Application Priority Data

Nov. 24, 1987 [DE] Fed. Rep. of Germany ....... 3739798  
Nov. 24, 1987 [DE] Fed. Rep. of Germany ....... 3739799

[51] Int. Cl.$^5$ ............................................. C07C 211/00  
[52] U.S. Cl. ..................................... 564/315; 526/937; 564/330; 564/335; 568/933  
[58] Field of Search ......................... 564/330, 335, 315

Primary Examiner—Robert V. Hines

[57] ABSTRACT

Compounds of the formula

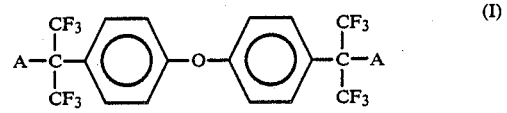

(I)

in which A represents the radicals

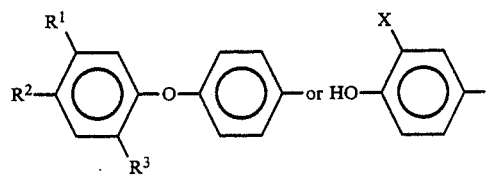

in which $R^1$ and $R^2$ are different from one another and denote hydrogen, —$NO_2$ or —$NH_2$, $R^3$ is hydrogen or halogen, X represents —$NO_2$ or —$NH_2$, with the proviso that $R^1$ is hydrogen, if $R^2$ is —$NO_2$ or —$NH_2$ and $R^2$ is hydrogen, if $R^1$ is —$NO_2$ or —$NH_2$.

The compounds are prepared from 4,4′-bis[2-(4-hydroxyphenyl)hexafluoroisopropyl]diphenyl ether by nitration or reaction with nitrobenzenes followed by reduction of the nitro groups. They are used for the preparation of high-temperature-resistant polycondensates.

6 Claims, No Drawings

4,4'-BIS[2-(4-HYDROXY-AMINO-PHENYL)HEXAFLUOROISOPROPYL]-DIPHENYLETHERS AND THEIR USE

The invention relates to novel fluoro-containing compounds based on 4,4'-bis[2-(4-hydroxyphenyl)hexafluoroisopropyl]diphenyl ether, processes for their preparation and their use, the compounds having two hexafluoroisopropylidene groups.

Fluoro-containing compounds, specifically fluoro-containing diamino compounds based on 2,2-bis[(3- or 4-aminophenoxy)phenyl]hexafluoropropane are known (U.S. Pat. No. 4,111,906 and EP-A No. 0,192,480). Compounds which have a halogen atom in the 2-position on the phenoxy ring are also known (U.S. Pat. No. 4,521,623). Those compounds which have a single hexafluoroisopropylidene group are used for the preparation of polyimides and polyamides having favorable properties such as thermal stability, resistance to irradiation and mechanical strength. It was therefore surprising that polymers having improved properties can be prepared from compounds having two hexafluoroisopropylidene groups in the molecule.

The invention relates to novel compounds based on 4,4'-bis[2-(4-hydroxyphenyl)hexafluoroisopropyl]-diphenyl ether of the formula

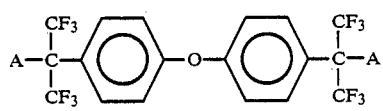 (I)

in which A represents the radicals

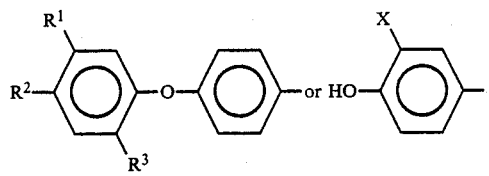

in which $R^1$ and $R^2$ are different from one another and denote hydrogen, $-NO_2$ or $-NH_2$, $R^3$ is hydrogen or halogen, X represents $-NO_2$ or $NH_2$, with the proviso that $R^1$ is hydrogen, if $R^2$ is $-NO_2$ or $-NH_2$ and $R^2$ is hydrogen, if $R^1$ is $-NO_2$ or $-NH_2$.

The invention also relates to a process for the preparation of compounds of the formula (I) and the use of the diamino compounds obtained therefrom.

The starting material for the novel, fluoro-containing compounds of the formula (I) is the 4,4'-bis[2-(4-hydroxyphenyl)hexafluoroisopropyl]diphenyl ether, which is converted to the corresponding dinitro compounds with aromatic, if desired halogen-containing, nitro compounds or by nitration. Chlorine is preferred as halogen. Preferably, the aromatic nitro compounds used are 4-chloronitrobenzene, 3,4-dichloronitrobenzene and 1,3-dinitrobenzene. The ratio of diphenyl ether to aromatic nitro compounds is in general 1:(2 to 3), preferably 1:(2.1 to 2.4), based on molar amounts. The 4-hydroxyphenyl compound used can be obtained by a process which has been described in the German Patent Application P No. 3,739,795.8, title: "Partially fluorinated diphenyl ethers, processes for their preparation and their use" submitted on the same day.

The reaction with the halogen-containing nitro compounds carried out in organic solvents, that is, in dipolar aprotic solvents such as dimethylformamide, dimethylacetamide, dimethyl sulfoxide, dimethyl sulfone, sulfolane or N-methyl-2-pyrrolidone.

At least stoichiometric amounts of a basic compound, for example alkali metal hydroxides such as sodium hydroxide or potassium hydroxide, ammonium hydroxide, alkali metal hydrides, alkali metal carbonates or alkaline earth metal carbonates such as sodium carbonate, potassium carbonate, sodium bicarbonate or potassium bicarbonate and also alkali metal alcoholates or mixtures are used in the reaction. The molar ratios are in general 1:(2 to 4), preferably 1:(2.1 to 3), based on diphenyl ether.

The reaction is in general carried out at a temperature of 50° to 200° C., preferably 100° to 180° C.

The nitration of 4,4'-bis[2-(4-hydroxyphenyl)hexafluoroisopropyl]diphenyl ether is carried out by conventional methods. In the nitration, the nitro group is selectively introduced at the ortho-position with respect to the hydroxyl group.

The nitration reaction can be carried out by using generally conventional nitrating acid mixtures, for example nitric acid with sulfuric acid, nitric acid with glacial acetic acid, nitric acid with acetic anhydride or nitric acid with water. In general, highly concentrated, anhydrous acid mixtures are used; however, 98% strength nitric acid is preferably used for the nitration reaction. The reaction is carried out in such a manner that the starting compound is dissolved in an organic solvent, for example tetrahydrofuran, dioxane, glacial acetic acid, ethanol or mixtures, but preferably diethyl ether, and the nitrating acid mixture is slowly added at a temperature of −10° to +50° C., preferably 5°–15° C. The workup is carried out by conventional methods. The novel dinitro compounds obtained in the first step can be reduced to the corresponding diamino compounds by conventional catalytic methods using hydrogenation catalysts or by stoichiometric methods, for example with tin(II) chloride/glacial acetic acid, in a second reaction step. In general, the isolated nitro compounds are hydrogenated, all of the hydrogenation by the stoichiometric method can also be carried out without isolating the compound.

Catalysts which can be used for the catalytic reduction are for example platinum metals, copper, iron, cobalt, nickel, mixtures thereof or metal oxides at atmospheric or superatmospheric pressure. Palladium is preferred. The catalyst can be used as the metal itself or in a finely divided form on surfaces such as carbon, barium sulfate, silica gel, aluminum and zeolite. The use of Raney nickel is also possible. The reduction takes place in organic solvents, for example alcohols such as methanol, ethanol and isopropyl alcohol, glycol such as ethylene glycol and propylene glycol, ethers such as diethyl ether, dioxane, tetrahydrofuran and ethylene glycol monomethyl or monoethyl ether, aliphatic hydrocarbon such as hexane and cyclohexane, aromatic hydrocarbons such as benzene, toluene and xylene, esters such as ethyl acetate and butyl acetate, halogenated hydrocarbons and also dimethylformamide and dimethyl sulfoxide. The temperatures in this reaction are in general between 10° and 130° C., preferably between 20° to 80° C., in particular between 20° and 60° C.

The diamino compounds obtained in the second step are suitable for the preparation of high-temperature-resistant polycondensates. Reaction with tetracarboxylic acids or derivatives thereof gives polyimides having, for example, low dielectric constants. On the other hand, the reaction with dicarbonyl chlorides gives polyamides. Furthermore, novel monomers and oligomers can be obtained, for example by reaction with dianhydrides. The imide monomers and oligomers obtained can be cured by addition reaction The amides according to the invention are furthermore suitable for the preparation of polymer precursors, epoxy resin curing agents, matrix resins, laminates, films, fibers, adhesives, coatings, photoresists and shaped articles.

It is known to prepare polyamides which have extraordinary physical and chemical properties from an organic diamine which was present as an aromatic tetravalent radical and in which each amino group is directly bound to a carbon atom of an aromatic ring, it being possible for an OH group to be in the ortho- or peri-position with respect to this carbon atom and which is reacted with a halogen-substituted dicarboxylic acid, an anhydride, lower alkyl esters or vinyl esters of this carboxylic acid (U.S. Pat. No. 3,449,296). Shaped articles can be prepared from the resulting polymeric hydroxyamides by conventional methods; however, they can also be converted to the corresponding polybenzoxazoles by a heat treatment with the elimination of water. The 4,4'-bis[2-(3-amino-4-hydroxyphenyl)hexafluoroisopropyl]diphenyl ether according to the invention can also serve as monomer for such polyamides and polybenzoxazoles.

EXAMPLES

(1)
4,4'-bis[2-(4-(4-nitrophenoxy)phenyl)hexafluoroisopropyl]diphenyl ether 13.1 g of 4,4'-bis[2-(4-hydroxyphenyl)hexafluoroisopropyl]diphenyl ether, 50 ml of dimethylacetamide, 20 ml of toluene, 1.8 g of NaOH and 3 ml of water are heated to reflux until no more water was separated in the water separator. The toluene was then distilled off, and the reaction mixture, after the addition of 7.1 g of 4-chloronitrobenzene, was heated to reflux for 24 hours. After the reaction mixture had been cooled to 25° C., the solid components were filtered off and discarded. The dimethylacetamide was separated off from the filtrate by distillation under reduced pressure, and the residue was recrystallized from acetonitrile. 12.5 g (71% of theory) of a beige-colored solid which melted at 160° C. remained Analysis by nuclear magnetic resonance spectroscopy gave the following values:

$^1$H-NMR (CDCl$_3$)δ(ppm): 8.2–8.3 m 4H, 7.15–7.5 m 8H, 7.0–7.1 m 12H; $^{19}$F-NMR (CDCl$_3$)δ(ppm): −64.4, s.

Analysis for C$_{24}$H$_{24}$F$_{12}$N$_2$O$_7$: Calculated: C 56.26, H 2.70, F 25.43, N 3.13, O 12.49. Found: C 55.70, H 2.60, F 25.30, N 2.90, O 12.40.

(2)
4,4'-bis[2-(4-(4-aminophenyl)phenyl-hexafluoroisopropyl]diphenyl ether 19 g of 4,4'-bis[2-(4-(4-nitrophenoxy)phen-yl)hexafluoroisopropyl]diphenyl ether were dissolved in 250 ml of ethyl acetate and, with the addition of 1 g of palladium and carbon (5% Pd content) reduced in a 1 l autoclave with hydrogen (100 bar) at 25°–30° C.). After the reduction, the catalyst was filtered off, and the solvent was distilled off. The crude product (18.1 g) was dissolved with heating in a solution consisting of octane/toluene (19/1) and treated with 3 g of activated carbon. The pale yellow solution was again completely concentrated, and the residue recrystallized from toluene. Yield: 15.4 g (85% of theory) pale yellow solid, m.p. 91°–93° C.

Nuclear magnetic resonance spectroscopy: $^1$H-NMR (CDCl$_3$)δ(ppm): 7.4–6.6 m 24H, 3.5 broad s 4H $^{19}$F-NMR (CDCl$_3$)δ(ppm): −64.6 s.

Analysis for C$_{42}$H$_{28}$F$_{12}$N$_2$O$_3$: Calculated: C 60.29, H 3.37, F 27.25, N 3.35, O 5.74. Found: C 60.20, H 3.20 F 26.80 N 3.50, O 5.80.

(3) 4,4'-bis[2-(4-(3-nitrophenoxy)phenyl)hexafluoroiso propyl]diphenyl ether 196 g of 4,4'-bis[2-(4-hydroxyphenyl)hexafluoroisopropyl]diphenyl ether were dissolved in 1000 ml of dimethylformamide and, after the addition of 120 g of 1,3-dinitrobenzene and 114 g of potassium carbonate, heated to reflux for 8 hours. The cooled reaction mixture was stirred into 10 l of water and, after the addition of 10 ml of concentrated hydrochloric acid, filtered. The solid which was separated off was thoroughly washed with water. Yield: 217 g (81% of theory) light brown solid, m.p.: 105°–107° C.

Nuclear magnetic resonance spectroscopy: $^1$H-NMR (CDCl$_3$)δ(ppm): 7.0–7.1 m 8H, 7.3–7.5 m 12H, 7.9–8.0 m 4H. $^{19}$F-NMR (CDCl$_3$)δ(ppm): −64.47 s

(4) 4,4'-bis[2-(4-(3-aminophenoxy)phenyl)hexafluoroiso propyl]diphenyl ether 89 g of 4,4'-bis[2-(4-(3-nitrophenoxy)phenyl)hexafluoroisopropyl]diphenyl ether were dissolved in 3000 ml of ethanol and reduced in a steel autoclave after the addition of 2 g of palladium on carbon (5%) at 50° C. with hydrogen (100 bar). After the catalyst had been filtered off, the solvent was completely distilled off. The crude product was dissolved in methanol and treated several times with activated carbon at the boiling temperature. Yield: 54 g (64% of theory) pale yellow solid, m.p.: 74°–77° C.

Nuclear magnetic resonance spectroscopy: $^1$H-NMR (CDCl$_3$)δ(ppm): 3.6 broad s 4H, 6.4–6.5 m 6H, 6.9–7.1 m 12H, 7.2–7.4 m 6H. $^{19}$F-NMR (CDCl$_3$)δ(ppm): −64.5 s.

Analysis for C$_{42}$H$_{28}$F$_{12}$N$_2$O$_3$: Calculated: C 60.29, H 3.27, F 27.25, N 3.35, O5.74. Found C 60.70, H 3.30, F 26.80, N 3.60, O 6.20.

(5)
4,4'-bis[2-(4-(2-chloro-4-nitrophenoxy)phenyl)hexafluoroisopropyl]diphenyl ether 39.2 g of 4,4'-bis[2-(4-hydroxyphenyl)hexafluoroisopropyl]-diphenyl ether were dissolved in 250 ml of dimethylformamide and heated to reflux for 4 hours after the addition of 25 g of 3,4-dichloronitrobenzene and 22 g of potassium carbonate. The cooled reaction mixture was added dropwise to 1000 ml of water and, after the addition of 10 ml concentrated hydrochloric acid, filtered. The solid which was separated off was washed with water and, after drying, recrystallized from acetonitrile. Yield: 37 g (64% of theory), m.p.: 154°–156° C.

Nuclear magnetic resonance spectroscopy: $^1$H-NMR (CDCl$_3$)δ(ppm): 7.0–7.1 m 10H, 7.4–7.5 m 8H, 8.1–8.2 2d 2H, 8.4 d 2H, $^{19}$F-NMR (CDCl3)δ(ppm): −64.5 s.

(6) 4,4'-bis[2-(4-(4-amino-2-chlorophenoxy)phenyl)hexafluoroisopropyl]diphenyl ether 29 g of 4,4'-bis[2-(4-(2-chloro-4-nitrophenoxy)phenyl)hexafluoroisopropyl]diphenyl ether were dissolved in 300 ml of ethyl acetate and, after the addition of 1 g of palladium on carbon (5%) reduced in a steel autoclave with hydrogen (100 bar) at 50° C. After the catalyst had been separated off, the ethyl acetate was completely separated off on a rotary evaporator. The crude product was stirred into 30 ml of dilute hydrochloric acid and recrystallized from ethanol, during which the solution was treated with activated carbon at the boiling temperature. After the reaction mixture had been cooled to 10° C., the white precipitate was filtered off, washed with water and suspended in 400 ml of water. The suspension was neutralized with dilute ammonia solution, the solid subsequently filtered off and washed with water. Yield: 21 g (72% of theory) white solid, m.p.: 93°–95° C.

Nuclear magnetic resonance spectroscopy. $^1$H-NMR (CDCl$_3$)δ(ppm): 3.5 broad s 4H, 6.5–6.6 2d 2H, 6.8–7.4 m 20H. $^{19}$F-NMR (CDCl$_3$)δ(ppm): −64.5 s (7) 4,4'-bis[2-(4-hydroxy-3-nitrophenyl)hexafluoroisopropyl]diphenyl ether 131 g of 4,4'-bis[2-(4-hydroxyphenyl)hexafluoroisopropyl]-diphenyl ether were disolved in 700 ml of dimethyl ether, and 76 ml of concentrated nitric acid was added dropwise at 10° C. The reaction mixture was stirred for 1 hour, and then poured onto 300 ml of a water/ice mixture. The organic phase was separated off, washed with cold saturated sodium bicarbonate solution until neutral, washed once with water and dried over magnesium sulfate. After the solvent had been separated off, 123 g (83% of theory) of a pale yellow solid remained m.p.: 67°–70° C.

Nuclear magnetic resonance spectroscopy gave the following values: $^1$H-NMR (CDCl$_3$)δ(ppm): 7–7.75 m 12H, 8.25 d 2H, 10.7 2H $^{19}$F-NMR (CDCl$_3$)δ(ppm): −64.6 s (8) 4,4'-bis[3-amino-4-hydroxyphenyl)hexafluoroisopropyl]diphenyl ether 150 g of 4,4'-bis[2-(4-hydroxy-3-nitrophenyl)hexafluoroisopropyl]diphenyl ether were dissolved in 1000 ml of ethanol and, after the addition of 4 g of palladium on carbon (10% Pd content), reduced in a 2 l autoclave with hydrogen (100 bar) at 25° C. After the reduction, the catalyst was filtered off, and the solvent was distilled off on the rotary evaporator. The crude product was purified by recrystallizing it twice from toluene. Yield: 82 g (60% of theory) white-grey solid, more than 99.5% pure by gas chromatography. m.p.: 208°–209° C.

Analysis for $C_{30}H_{20}F_{12}N_2O_3$ Calculated: C 52.64, H 2.95, N 4.09, O 7.01, F 33.31. Found: F 52.90, H 3.00, N 4.10, O7.20, F 33.50.

Nuclear magnetic resonance spectroscopy: $^1$H-NMR (CDCl$_3$)δ(ppm): 9.3–10.0 broad s 2H, 7.1–7.5 m 8H, 6.3–6.8 m 6H, 4.8 broad s 4H. $^{19}$F-NMR (CDCl$_3$)δ(ppm): −67.7 s.

We claim:

1. A compound of the formula

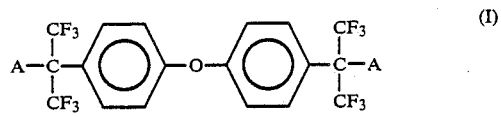

(I)

in which A represents the radicals

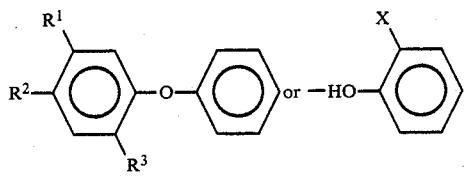

in which $R^1$ and $R^2$ are different from one another and denote hydrogen, or —NH$_2$, $R^3$ is hydrogen or halogen, X represents —NH$_2$, with the proviso that $R^1$ is hydrogen, if $R^2$ is —NH$_2$ and $R^2$ is hydrogen, if $R^1$ is —NH$_2$.

2. The compound as claimed in claim 1, wherein the halogen is chlorine.

3. A compound of the formula

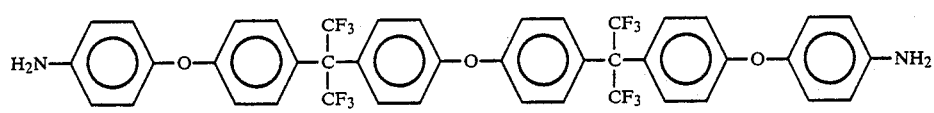

4. A compound of the formula

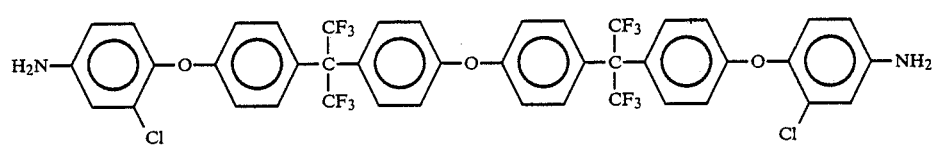

5. A compound of the formula

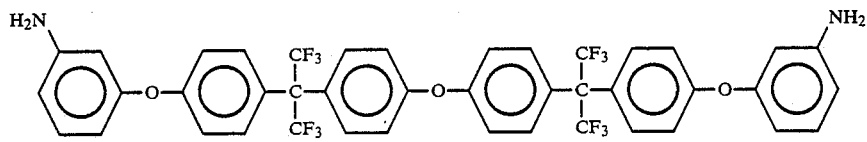

6. 4,4'-bis[2-(3-amino-4-hydroxyphenyl)hexafluoroisopropyl]-diphenyl ether.

* * * * *